US012193664B1

(12) United States Patent
Shelton, IV et al.

(10) Patent No.: US 12,193,664 B1
(45) Date of Patent: Jan. 14, 2025

(54) MOTOR CONTROL OF SURGICAL STAPLER WITH CONTROLLED IMPACT AT END OF FIRING STROKE

(71) Applicant: CILAG GMBH INTERNATIONAL, Zug (CH)

(72) Inventors: Frederick E. Shelton, IV, Hillsboro, OH (US); Shane R. Adams, Lebanon, OH (US); Jason L. Harris, Lebanon, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 0 days.

(21) Appl. No.: 18/481,014

(22) Filed: Oct. 4, 2023

(51) Int. Cl.
*A61B 17/072* (2006.01)
*A61B 17/068* (2006.01)
*A61B 34/30* (2016.01)
*A61B 90/00* (2016.01)
*A61B 17/00* (2006.01)
(Continued)

(52) U.S. Cl.
CPC .......... *A61B 17/072* (2013.01); *A61B 17/068* (2013.01); *A61B 17/07207* (2013.01); *A61B 34/30* (2016.02); *A61B 90/03* (2016.02); *A61B 2017/00017* (2013.01); *A61B 17/00234* (2013.01); *A61B 2017/00398* (2013.01); *A61B 2017/07214* (2013.01); *A61B 2017/07271* (2013.01); *A61B 17/29* (2013.01); *A61B 34/71* (2016.02); *A61B 2090/034* (2016.02); *A61B 90/98* (2016.02)

(58) Field of Classification Search
CPC ............... A61B 17/068; A61B 17/072; A61B 17/07207; A61B 17/105; A61B 17/115; A61B 17/29; A61B 17/295; A61B 17/32; A61B 34/30; A61B 34/37; A61B 34/70; A61B 34/71; A61B 34/76; A61B 90/03; A61B 90/06; A61B 90/361; A61B 90/98; A61B 2017/00017; A61B 2017/00022; A61B 2017/07214; A61B 2017/07271; A61B 2017/00398
USPC .............. 227/19, 175.1, 175.2, 176.1, 180.1; 606/1, 130, 139, 167, 219
See application file for complete search history.

(56) References Cited

U.S. PATENT DOCUMENTS 6,565,554 B1 * 5/2003 Niemeyer ............... A61B 34/37
606/1
9,002,518 B2 * 4/2015 Manzo ................... A61B 90/98
901/19
(Continued)

*Primary Examiner* — Scott A Smith
(74) *Attorney, Agent, or Firm* — TROUTMAN PEPPER HAMILTON SANDERS LLP

(57) ABSTRACT

A software for driving a motor in a powered surgical stapler can include a pausing monitoring process that may be effective to improve staple form and/or increase localized compression of tissue. The pausing monitoring process monitors firing speed of a firing bar driving by the motor and pauses the motor when the firing speed passes a speed error threshold. Before pausing the motor, the pausing monitoring process may also require that a pulse width modulated (PWM) electrical signal driving the motor has a duty cycle over a duty cycle threshold while the firing speed is beyond the speed error. The pausing monitoring process may force the firing bar through a predetermined distance immediately after pausing. The pausing monitoring process may be limited in the number of pauses that can be taken during a firing stroke.

20 Claims, 8 Drawing Sheets

(51) Int. Cl.
    *A61B 17/29*     (2006.01)
    *A61B 34/00*     (2016.01)
    *A61B 90/98*     (2016.01)

(56) References Cited

U.S. PATENT DOCUMENTS

| | | | |
|---|---|---|---|
| 9,307,986 B2 | 4/2016 | Hall et al. | |
| 9,615,888 B2 * | 4/2017 | Manzo | A61B 34/74 |
| 9,808,246 B2 | 11/2017 | Shelton, IV et al. | |
| 10,307,170 B2 | 6/2019 | Parfett et al. | |
| 10,441,279 B2 * | 10/2019 | Shelton, IV | A61B 17/295 |
| 10,695,058 B2 | 6/2020 | Lytle, IV et al. | |
| 10,828,028 B2 | 11/2020 | Harris et al. | |
| 11,090,046 B2 | 8/2021 | Shelton, IV et al. | |
| 11,376,002 B2 | 7/2022 | Shelton, IV et al. | |
| 11,395,652 B2 | 7/2022 | Parihar et al. | |
| 11,517,311 B2 | 12/2022 | Lytle, IV et al. | |
| 11,666,332 B2 | 6/2023 | Giordano et al. | |
| 2011/0295269 A1 * | 12/2011 | Swensgard | A61B 34/76 606/130 |
| 2012/0239067 A1 * | 9/2012 | Whitman | A61B 17/07207 606/167 |
| 2012/0310254 A1 * | 12/2012 | Manzo | A61B 17/072 606/130 |
| 2017/0296213 A1 * | 10/2017 | Swensgard | A61B 17/32 |
| 2022/0378425 A1 | 12/2022 | Huang et al. | |
| 2023/0048444 A1 | 2/2023 | Shelton, IV et al. | |

\* cited by examiner

MOTOR CONTROL OF SURGICAL STAPLER WITH CONTROLLED IMPACT AT END OF FIRING STROKE

FIELD

This application relates generally to medical devices, and in particular to motor driven surgical staplers.

BACKGROUND

Innovation in surgical stapling technology has evolved from manual to power-operated staplers. Manual staplers clamp tissue, deliver staples, and drive a knife blade through mechanical force applied to lever(s) on a handle of the stapler. Powered staplers use an electrically powered motor to drive the knife blade and staples. Powered staplers may also use an electrically powered motor to clamp tissue. Upon their introduction, powered staplers delivered staples with fixed motor drive without regard to tissue properties. Many surgical stapling challenges relate to tissue dynamics, tissue movement, and tissue variability. Different tissue types present unique tissue challenges. Firing algorithms have been disclosed in which motor drive is varied with time to address the unique tissue challenges. For instance, U.S. Pat. No. 9,808,246 discloses a method of operating a powered surgical instrument; U.S. Pat. No. 10,307,170 discloses a method for closed loop control of motor velocity of a surgical stapler; U.S. Pat. No. 10,828,028 discloses a surgical instrument with multiple program responses during a firing motion; U.S. Pat. No. 11,090,046 discloses systems and methods for controlling displacement member motion of a surgical stapler; U.S. Pat. No. 11,517,311 discloses a surgical instrument comprising an articulatable end effector and means for adjusting the firing stroke of a firing member; U.S. Patent Pub. No. 2023/0048444 discloses a variable response motor control algorithm for a powered surgical stapler; and U.S. Patent Pub. No. 2022/0378425 discloses a control system that controls firing stroke length, each of which are incorporated by reference as if set forth in their entireties herein.

SUMMARY

Examples disclosed herein generally describe software for driving a motor in a powered surgical stapler to provide consistent staple stroke length. The software includes a firing stroke algorithm that calls an end of stroke algorithm configured to slow a firing speed of a firing assembly near the end of the stroke and intentionally impact a distal portion of the firing assembly to a fixed distal feature of the end effector of the surgical stapler at the completion of the stroke.

The end of stroke algorithm may further be configured to provide a motor control signal based on identification of configuration of the end effector. The end of stroke algorithm can be compatible with other firing speed control algorithms such that firing speed can be controlled by the other firing speed control algorithm at the beginning and through the middle of the firing stroke, then the firing speed can be controlled by the end of stroke algorithm over a short distance at the end of the firing stroke. Examples disclosed herein further include a surgical stapler configured with the end of stroke algorithm and configured to withstand mechanical impact of a distal portion of a firing assembly to a fixed distal feature of the end effector.

In one embodiment, a powered surgical stapler includes a firing assembly, a motor assembly, and a speed control circuit. The firing assembly is configured to translate along a longitudinal axis such that translation of the firing assembly in a distal direction, during a firing stroke, is configured to deploy staples from an end effector. The motor assembly is mechanically coupled to the firing assembly and configured to drive the firing assembly along the longitudinal axis. The speed control circuit is configured to drive the firing assembly to an initial target speed through an initial distance of the firing stroke, drive the firing assembly to an increased target speed through a middle distance of the firing stroke that is distal to the initial distance such that the increased target speed is greater than the initial target speed, drive the firing assembly to a decreased target speed through a final distance of the firing stroke that is distal to the middle distance such that the decreased target speed is less than the increased target speed, detect an impact of a distal portion of the firing assembly to the end effector, and cease driving the firing assembly in response to the detection of the impact.

In one embodiment, a method for controlling a firing stroke of a surgical stapler includes the following steps that can be carried out in various orders. The method can include driving the firing assembly to an initial target speed through an initial distance of the firing stroke. The method can include driving the firing assembly to an increased target speed through a middle distance of the firing stroke that is distal to the initial distance such that the increased target speed is greater than the initial target speed. The method can include driving the firing assembly to a decreased target speed through the final distance of the firing stroke that is distal to the middle distance such that the decreased target speed is less than the increased target speed. The method can include detecting an impact of a distal portion of the firing assembly to the end effector. The method can include ceasing the driving of the firing assembly in response to detecting of the impact. The method can include additional compatible steps as understood by a person skilled in the pertinent art.

BRIEF DESCRIPTION OF THE DRAWINGS

While the specification concludes with claims, which particularly point out and distinctly claim the subject matter described herein, it is believed the subject matter will be better understood from the following description of certain examples taken in conjunction with the accompanying drawings, in which like reference numerals identify the same elements. The figures depict one or more implementations of the inventive devices, by way of example only, not by way of limitation.

DETAILED DESCRIPTION

Figure 1:
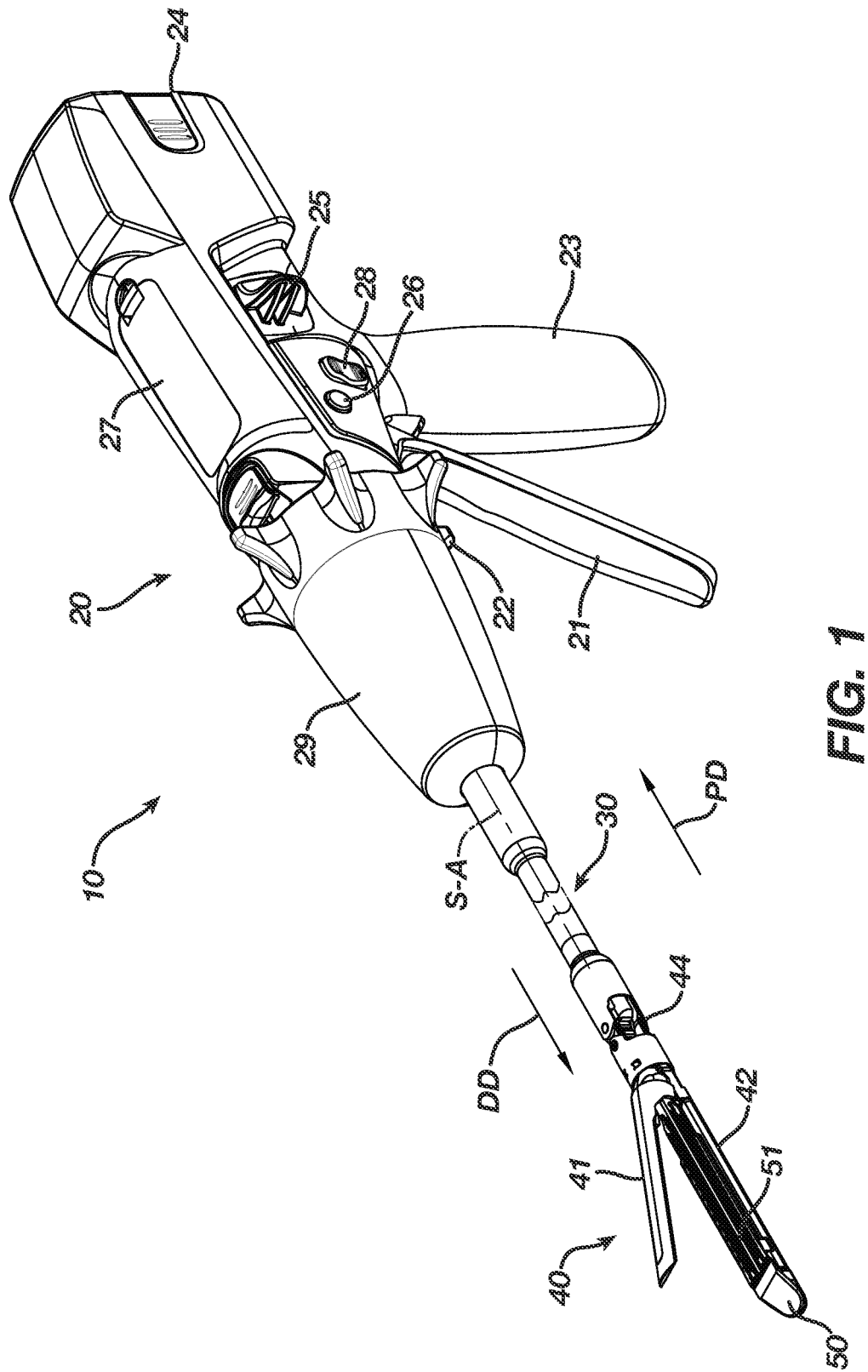
FIG. 1 is a perspective view of an exemplary powered surgical stapler.

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives, and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g., "about 90%" may refer to the range of values from 81% to 99%.

As used herein, the terms "patient," "host," "user," and "subject" refer to any human or animal subject and are not intended to limit the systems or methods to human use, although use of the subject invention in a human patient represents a preferred embodiment. As well, the term "proximal" indicates a location closer to the operator whereas "distal" indicates a location further away to the operator or physician.

As used herein, the terms "memory" and "non-transitory computer-readable media" are used interchangeable and are understood to include, but are not limited to, random access memory (RAM), read-only memory (ROM), electronically erasable programmable ROM (EEPROM), flash memory or other memory technology, compact disc ROM (CD-ROM), digital versatile disks (DVD) or other optical storage, magnetic cassettes, magnetic tape, magnetic disk storage or other magnetic storage devices, or any other tangible, physical medium which can be used to store computer readable information.

Alternative apparatus and system features and alternative method steps are presented in example embodiments herein. Each given example embodiment presented herein can be modified to include a feature and/or method step presented with a different example embodiment herein where such feature and/or step is compatible with the given example as understood by a person skilled in the pertinent art as well as where explicitly stated herein. Such modifications and variations are intended to be included within the scope of the claims.

Examples disclosed herein generally describe software for driving a motor in a powered surgical stapler to provide consistent stroke length. The surgical stapler includes a firing assembly driven by a motor assembly. The firing assembly includes elongated structures extending through a shaft of the surgical stapler that shift and/or bend during operation of the surgical stapler. Motor control is in a proximal direction in relation to the shaft (e.g., in a handle of the surgical stapler).

While measurement of motor rotation can provide an approximate location of a distal end of the firing assembly, some uncertainty in position of the distal end of the firing assembly may occur during a firing stroke due to the shifting and/or bending of the elongated structures of the firing assembly. For instance, articulation of the end effector may cause a firing rod of the firing assembly to bend so that the distal portion of the firing assembly travels a shorter distance through the firing stroke compared to when the end effector is aligned along the longitudinal axis of the shaft. The surgical stapler may be configured with switches, triggers, or other sensors on the end effector to measure position of the distal portion of the firing assembly more directly; however, a consistent stopping position may nevertheless be difficult to achieve due to inertia of the firing assembly, dynamic breaking ability of the motor, and resistance due to tissue or other load. Such factors may lead to uncertainty in firing stroke length regardless of articulation of the end effector.

The disclosed software includes an end of stroke algorithm that slows a firing speed of the firing assembly through a short distance near the end of the firing stroke and causes an intentional impact between a distal portion of a firing assembly and the end effector. Configured as such, the distal portion of the firing assembly is configured to consistently traverse through the firing stroke until stopped by impact to the end effector, regardless of articulation angle of the end effector, inertia of the firing assembly, dynamic breaking power of the motor, encountered tissue properties, or other factors which would otherwise result in inconsistent firing stroke length.

A stapler configured with the described software may provide reliable staple formation, deliver consistent results, support better patient outcomes, and/or provide other benefits. The software may be utilized with existing powered surgical stapler hardware such as the ECHELON™ 3000 and other contemporary powered surgical staplers. Additionally, or alternatively, the software may be compatible with older powered surgical staplers, robotic surgical staplers, or surgical stapler hardware yet to be developed. Such staplers are referred to generically herein as a "surgical stapler" or "powered surgical stapler." In some embodiments, the end effector may include an impact feature which includes a resistance member configured to apply smooth or gradual resistance and/or deceleration of the firing assembly. The resistance member may include a spring, bumper, elastomeric material, magnet, pulley, gear, or other such configuration. For instance, the resistance member may be configured with compatible features of a resistance member disclosed in U.S. Pat. No. 9,307,986 incorporated herein by reference.

The disclosed software includes a firing stroke algorithm which is configured to control motor speed from a beginning of the firing stroke to the end of the firing stroke. The firing stroke algorithm includes or calls the end of stroke algorithm such that the end of stroke algorithm controls motor speed through a final distance of the firing stroke.

In some embodiments, the firing stroke algorithm drives the firing assembly to an initial target speed and with an initial motor load threshold to minimize a likelihood of damaging the end effector in a lockout condition. In some embodiments, once the firing assembly has traversed an initial distance, the firing stroke algorithm increases the target speed above the initial speed and/or increases the motor load threshold. The firing stroke algorithm may maintain the increased target speed and increased motor load threshold through a majority of the firing stroke, and then engage the end of stroke algorithm for the final distance of the firing stroke.

The firing stroke algorithm can be adapted for use with a surgical stapler utilizing switch logic and/or closed loop feedback to determine position of the distal portion of the firing assembly. During a firing stroke, there may be uncertainty or variation in the position of the distal portion of the firing assembly as a result of using switch logic and/or closed loop feedback. The distance from the distal end of the stroke length at which the end of stroke firing algorithm is engaged can be positioned to account for this uncertainty or variation so that the firing assembly slows to the reduced target speed before impacting the end effector.

Variations in a firing stroke length can cause variations in cutline length. Additionally, when the firing stroke length is too short, staples at the distal end of the end effector may be under-formed or may not deploy. Variations in firing stroke length may arise due to tissue properties, articulation angle, or other causes disclosed herein and understood by a person skilled in the pertinent art. The end of stroke algorithm can be utilized to reduce or eliminate variables in firing stroke length. The end of stroke algorithm is configured to advance the distal portion of the firing assembly (e.g., sled and knife) to the same end position at the end of the firing stroke regardless of articulation angle, load on the end effector, encountered tissue properties, or other factors that may otherwise cause variation in firing stroke length.

FIG. 1 is a perspective view of an exemplary surgical stapler 10 including a handle 20, a shaft 30, and an end effector 40. The handle 20 is configured to be grasped, manipulated, and actuated by a clinician external to a patient. The shaft 30 is sized, shaped, and otherwise configured to extend through a body opening of the patient. The end effector 40 is configured to deliver staples 51 and (optionally, preferably) cut tissue within the body of the patient. The illustrated surgical stapler 10 can be configured with a firing stroke algorithm that controls the speed of a firing stroke to deliver staples (and optionally cut tissue) such that an end of stroke algorithm controls speed through a final distance of the firing stroke.

The handle 20 can include a closure trigger 21, a firing trigger 22, and a grip 23 sized such that a clinician can single-handedly hold the surgical stapler 10 by the grip 23 while manipulating the closure trigger 21 or the firing trigger 22. The closure trigger 21 is operably connected to a motor disposed within the handle 20 such that when the closure trigger 21 is pulled, the motor is driven to cause the end effector 40 to clamp tissue. The firing trigger 22 is operably connected to the motor (or alternatively an additional motor) disposed within the handle 20 such that when the firing trigger 22 is pulled, the motor is driven to cause the end effector 40 to deploy staples 51 into the clamped tissue and cut the clamped tissue.

The handle 20 can further include additional features such as a safety button (not illustrated) which can be manipulated to prevent actuation of the firing trigger 22, a power pack 24 configured to provide electrical power to the motor and other electrical components of the powered surgical stapler 10, a closure release button 25 which can be manipulated to release the end effector 40 and the closure trigger 21 from the clamped position, a home button 26 that can be pressed to cause the motor to move a knife 43 (FIG. 2) of the end effector 40 in the proximal direction PD to a home position X0 (FIG. 2), a manual override 27 including a mechanical actuator which can be manipulated to mechanically move the knife proximally to the home position, articulation buttons 28 that can be pressed to cause the motor (or alternatively one or more additional motors) to articulate the end effector 40 at an articulation joint 44 so that the end effector 40 is at an angle with a longitudinal axis S-A of the shaft 30 (FIG. 4), a rotatable nozzle 29 configured to be rotated so that the shaft 30 and end effector rotate about the shaft axis S-A, a display (not illustrated) configured to display information related to the surgical stapler, variations thereof, other compatible features of a powered surgical stapler handle, and combinations thereof.

The shaft 30 includes one or more elongated structures therein that can be moved longitudinally by rotation of rotor(s) of the motor(s) in the handle 20 to result in clamping of tissue by the end effector 40 and deployment of the staples 51.

The end effector 40 includes an anvil 41 and a staple jaw 42 opposite the anvil 41. Tissue (not illustrated) is clamped between the anvil 41 and staple jaw 42 when the end effector 40 is in the clamped configuration.

Portions of the surgical stapler 10 may be detachable and interchangeable. For instance, at least a portion of the shaft 30 including the end effector 40 may be detachable from the handle 20, and the handle 20 may be configured for use in connection with interchangeable shaft assemblies having different shaft lengths and/or different end effectors attached thereto. The end effector 40 may be detachable from the shaft 30, and the shaft 30-handle 20 combination may be configured for use in connection with interchangeable end effectors. Staples 51 may be housed in a staple cartridge 50 that is detachable from the end effector 40.

In some embodiments, the firing stroke algorithm utilizes an identification of a configuration of the end effector 40. For instance, the software can be configured to identify an installed staple cartridge 50 as disclosed in U.S. Pat. No. 11,376,002. The identification of the configuration of the end effector 40 can be used to define a speed and/or load limit change in motor control of the firing assembly. For instance, a configuration of a staple cartridge 50 (also referred to as a "reload" or "cartridge reload") of the end effector 40 can be identified, and the speed and/or load limit can be set or defined by the firing stroke algorithm based at least in part on the configuration of the staple cartridge 50. In some embodiments, the end of stroke algorithm is configured to set a target speed and/or load limit through the final distance of the firing stroke based at least in part on the identification of the configuration of the end effector 40. In some embodiments, the length of the final distance, i.e., position at which the end of stroke algorithm is engaged, is determined based at least in part on the identification of the configuration of the end effector 40. In some embodiments, the length of the final distance is set based at least in part on the cartridge type. In some embodiments, the firing stroke algorithm includes more than one displacement triggers that change operational properties of the motor, depending on the configuration of the sensed cartridge configuration.

In some embodiments, the surgical stapler 10 is configured to determine a length of a firing stroke (also referred to herein as "firing line length") of an end effector 40. For instance, for a non-modular endocutter, the firing line length of the end effector 40 can be pre-programmed into the firing stroke algorithm. As another example, for a modular surgical stapler, a cartridge reload 50 can have a predetermined firing line length, and the surgical stapler 10 can be configured to identify the cartridge reload 50. In some embodiments, the cartridge reload 50 is identified by radio frequency identification (RFID), one-wire chip, or other suitable detection. In some embodiments, the end of stroke algorithm is configured to reduce the firing speed near the end of the firing stroke proportionate to the backlash stopping distance and/or the inertia and allow the firing assembly to impact the given type of surgical stapler while also providing minimal damage to the staple cartridge 50 or surgical stapler 10.

In some embodiments, the end of stroke algorithm is adapted to cause the motor to stop the firing assembly in response to impact a distal portion of the end effector in a surgical stapler 10 that, without the benefit of the end of stroke algorithm, would become damaged as a result of the impact. For instance, a surgical stapler, lacking the end of stroke algorithm may have kinetic energy of the motor gearbox and drive train such that when impact of the firing assembly is detected (e.g., by rise in motor current) there is not enough time to rotor lock the motor and pull the drive train from movement to stop without damaging the end effector or other component of the surgical stapler. In such embodiments, the end of stroke algorithm can be applied to said surgical stapler to slow the firing assembly through a distal portion of the firing stroke to reduce the kinetic energy of the motor gearbox and drive train such that when impact of the firing assembly is detected, there is enough time to rotor lock the motor and pull the drive train from movement to stop without damaging the end effector or other component of the surgical stapler. For instance, the surgical stapler 10 may be configured to drive a firing assembly with approximately 200 lbs. of force at about a 500:1 gear ratio at about 17-25 mm/second with dynamic breaking configured to stop the momentum at this speed in about 2 to 5 mm of travel. In the given example surgical stapler 10, if the impact of the firing assembly to the end effector is detected at full speed, the motor may be incapable of sufficiently limiting kinetic energy out of the impact to avoid damage to the end effector. In the given example, the end of stroke algorithm may be used to control the surgical stapler to slow the motor speed near the end of the firing stroke. At a slower speed the detection of the impact is faster, and the kinetic energy is less, so the slower speed allows for both faster reactions, limiting more of the energy in the impact due to dynamic breaking, and having less overall kinetic energy to stop.

The end of stroke algorithm may be adaptable to many different types of end effector and firing assembly configurations without requiring complex calibration at manufacturing. The end of stroke algorithm may produce reliable cut line lengths and complete staple deployment without requiring calibration at multiple articulation angles for a given configuration of firing assembly and end effector. Rather, the end of stroke algorithm may be configured to adapt to various firing assembly and end effector configurations by simply determining an end of stroke region and end of stroke speed profile in which the firing assembly slows so that momentum of the firing assembly can be halted by the motor in response to impact of the firing assembly to a distal portion of the end effector, without damaging the device. In some embodiments, the end of stroke algorithm is configured to adapt to various end effector configurations based in part, or solely on end-effector or cartridge length.

The surgical stapler 10 can be modified to include various features to facilitate operation of the firing stroke algorithm disclosed herein as understood by a person skilled in the pertinent art.

Figure 2:
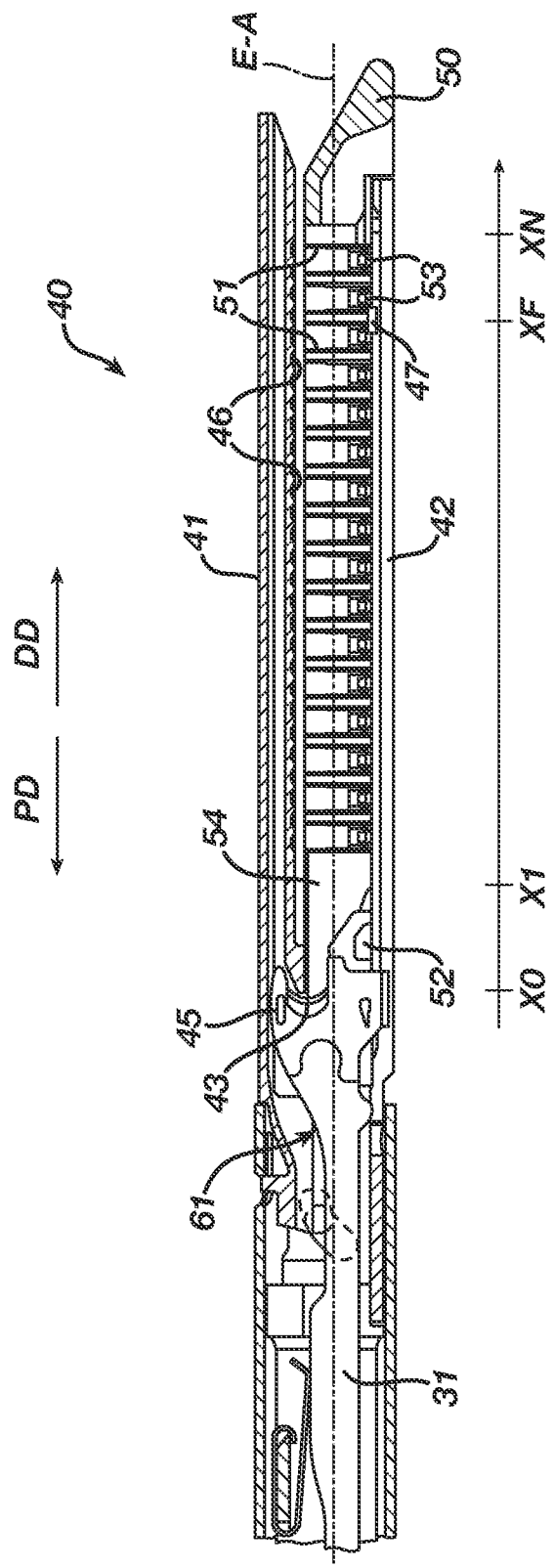
FIG. 2 is an illustration of an exemplary end effector of an exemplary powered surgical stapler.

FIG. 2 is a sectional view of the end effector 40 of the powered surgical stapler 10. The end effector 40 is in a clamped configuration and the knife 43 is at the home position X0 prior to a firing stroke. The staple cartridge 50 is attached to the staple jaw 42 and positioned within a cartridge channel 54. A firing bar 31 extends in the proximal direction PD into the shaft 30. The firing bar 31 is translatable in the distal direction DD and the proximal direction PD. A distal portion of the firing bar 31 moves through the end effector 40 along a longitudinal axis E-A of the end effector 40. When the end effector 40 is not articulated, the longitudinal axis E-A of the end effector 40 is in line with the shaft axis S-A (FIG. 1). An I-beam 45 is coupled to the knife 43 and the distal portion of the firing bar 31. A wedge sled 52 is positioned in the staple cartridge 50. As the I-beam 45 translates distally, the cutting edge of the knife 43 contacts and may cut tissue positioned between the anvil 41 and the staple cartridge 50. Also, the I-beam 45 contacts the wedge sled 52 and pushes it distally, causing the wedge sled 52 to contact staple drivers 53. The staple drivers 53 may be driven up into staples 51, causing the staples 51 to advance through tissue and into pockets 46 defined in the anvil 41, which shape the staples 51.

During a firing stroke, several components of the powered surgical stapler 10 translate longitudinally (i.e., along the shaft axis S-A and/or along the end effector axis E-A), including the firing bar 31, the knife 43, the I-beam 45, and the wedge sled 52. The components of the powered surgical stapler 10 which translate longitudinally during a firing stroke are collectively referred to herein as a firing assembly 61. A motor disposed within the handle 20 (FIG. 1) of the surgical stapler 10 is mechanically coupled to a proximal end of the firing assembly 61 so that rotation of the motor pushes the firing assembly 61 distally during a firing stroke. Elongated structures, such as the firing bar 31, may bend or otherwise deform during usage of the surgical stapler 10 causing variation in the position of distal features (e.g., knife 43, I-beam 45, and wedge sled 52) of the firing assembly 61 from one firing stroke to the next. Positions of the distal features (e.g., knife 43, I-beam 45, and wedge sled 52) of the firing assembly 61 may not be precisely determined based on degree of motor rotation or position of a proximal end of the firing assembly 61 during a firing stroke. The surgical stapler 10 can be configured with an end of stroke algorithm that slows a firing speed of the firing assembly 61 through a short distance near the end of the firing stroke and causes an intentional impact between a distal portion of a firing assembly 61 and the end effector 40.

The knife 43 and I-beam 45 are at the home position X0 before advancing through a firing stroke. During a firing stroke, the I-beam 45 and knife 43 move distally from the home position X0. The firing stroke is completed when the I-beam 45 and knife 43 arrive at the stroke end position XN. The length of the firing stroke is therefore the distance from the home position X0 to the end position XN.

The firing assembly 61 is driven by a motor 63 (FIGS. 6 and 7) coupled to a speed control circuit 71 (FIG. 6) configured with a firing stroke algorithm. The firing stroke algorithm is configured to set a target speed that changes during the firing stroke, and the speed control circuit 71 is configured to drive the motor 63 to the target speed set by the firing stroke algorithm.

In some embodiments, the firing stroke algorithm sets an initial target speed at which the speed control circuit 71 drives the distal portion of the firing assembly 61 from the home position X0 through an initial distance X1 of the firing stroke. In some embodiments, the firing stroke algorithm also utilizes an initial motor load threshold, and the speed control circuit 71 slows the firing stroke in the initial distance (X0 to X1) when the initial motor load threshold is met in order to reduce likelihood of damaging the end effector 40 in a lockout condition.

In some embodiments, the firing stroke algorithm sets an increased target speed through a middle distance of the firing stroke, from X1 to XF, such that the increased targets speed is greater than the initial target speed. In some embodiments, the firing stroke algorithm also utilizes a motor load threshold in the middle distance of the firing stroke. In embodiments in which a motor load threshold is utilized in the initial distance and in the middle distance, the motor load threshold may be greater in the middle distance. In some embodiments, the middle distance constitutes a majority of the length of the firing stroke. In some embodiments, the firing stroke algorithm maintains the increased target speed and increased motor load threshold through a majority of the firing stroke.

The firing stroke algorithm engages an end of stroke algorithm when the distal portion of the firing assembly 61 is at a position XF, that is a short distance from end position XN. The end of stroke algorithm sets a decreased target speed slows the firing speed of the firing assembly 61 through the short distance near the end of the firing stroke and causes the distal portion of the firing assembly 61 to intentionally impact the end effector 40. The end of stroke algorithm is configured to detect an impact of the distal portion of the firing assembly 61 to the end effector 40 and cease driving the firing assembly 61 in response to detection of the impact.

Additionally, or alternatively, the firing stroke algorithm may utilize one or more other speed control algorithms up until the end of stroke algorithm is utilized. Example suitable algorithms are included in U.S. Pat. Nos. 9,808,246, 10,307,170, 10,828,028, 11,090,046, 11,517,311, U.S. Patent Pub. No. 2023/0048444, and Patent Pub. No. 2022/0378425, each of which are incorporated by reference herein. The firing stroke algorithm may include a motor control algorithm yet to be developed or other speed control algorithm that is compatible with the end of stroke algorithm, as understood by a person skilled in the pertinent art. Such algorithms are preferably used through the middle portion of the firing stroke. The end of stroke algorithm may also utilize a speed-control algorithm that adjust the target speed based on impacts or other cutting resistance experienced prior to the impact at the end of the firing stroke. Impacts prior to the end of the firing stroke are treated differently than the impact at the end of the firing stroke.

The end effector 40 illustrated in FIG. 2 can be modified to include additional and/or alternative firing assembly components as understood by person skilled in the pertinent art. Further, the shaft 30 and/or handle 20 may include additional firing assembly components not illustrated herein as understood by a person skilled in the pertinent art.

In one embodiment, the end effector 40 includes a 60 mm cartridge reload 50, and the firing stroke algorithm utilizes a target speed (or speeds) and motor load threshold (or thresholds) through 0-55 mm of a firing stroke such that the start point XF of the end of stroke algorithm is 5 mm from the end position XN. Alternatively, the firing stroke algorithm may utilize any suitable firing algorithm through the first 0-55 mm of the firing stroke. Depending on the algorithm utilized during the majority of the firing stroke, the firing stroke algorithm may change the target speed and/or load threshold based on monitored speed, momentum, tissue thickness, exerted force, other such parameter, or sub combination thereof. In the last 5 mm of the firing stroke, the firing stroke algorithm engages the end of stroke algorithm, which reduces the target speed to a much lower speed and also reduces a force limit threshold or other load threshold. The lower speed and load threshold can be configured for a predefined collision impact of a distal portion of the firing assembly 61 (e.g., I-beam 45 and/or wedge sled 52) with the end effector 40 to signify that the firing assembly 61 is fully extended.

The end of stroke algorithm may be adaptable to function with existing powered surgical stapler hardware such as the ECHELON™ 3000 and other contemporary powered surgical staplers. Additionally, or alternatively, the software may be compatible with older powered surgical staplers, robotic surgical staplers, or surgical stapler hardware yet to be developed. For instance, the end of stroke algorithm may be adaptable to function with a powered surgical stapler that does not need to be mechanically modified in order to absorb the impact between the end effector 40 and distal portion of the firing assembly 61. The feature(s) of the distal portion of the firing assembly 61 and the feature(s) of the end effector 40 that impact each other at the end of the firing stroke are referred to herein as "impact features." In some embodiments, a portion of the I-beam 45 impacts a distal end of a channel slot (not illustrated) in the staple jaw 42 and/or anvil 41. In some embodiments, a distal end of the wedge sled 52 is intended to impact the staple cartridge 50. Alternatively, the end effector 40 and/or firing assembly 61 can include impact feature(s) having one or more resistance members configured to apply smooth or gradual resistance and/or deceleration of the firing assembly upon impact between the distal portion of the firing assembly 61 and end effector 40. The resistance member may include a spring, bumper, elastomeric material, magnet, pulley, gear, or other such configuration. For instance, the resistance member may be configured with compatible features of a resistance member disclosed in U.S. Pat. No. 9,307,986 incorporated herein by reference.

In some embodiments, the end effector 40 includes a switch 47 configured to close in response to the distal portion of the firing assembly 61 encountering the switch 47 during the firing stroke. The switch 47 can be configured similar to such switches in the Echelon Powered Flex or powered stapler utilizing switch logic. The firing stroke algorithm can be configured to engage the end of stroke algorithm in response to receiving an electrical signal from the switch 47 indicating closure of the switch 47. The switch logic may introduce longitudinal instability of the timing and consistency of the switch 47. At typical firing speeds through the middle portion of the firing stroke, and under various use conditions, the distal portion of the firing assembly 61 may travel 0.005"-0.020" (0.1 mm-0.5 mm) distally beyond the switch 47 before the motor 63 (FIGS. 6 and 7) responds to the closure of the switch 47. In some embodiments, the start position XF of the end of stroke algorithm is determined at least in part on variation in closure timing of the switch 47 to account for the variation in travel of the distal portion of the firing assembly 61.

The firing assembly 61, transmission 66 (FIGS. 6 and 7), and motor 63 (FIGS. 6 and 7) have inertia that affects acceleration and deceleration of the firing assembly 61 during a firing stroke. The speed of the motor and inertia of the firing assembly 61, gearing, and motor define impact capacity at the end of the firing stroke. Components that affect inertia may include an I-beam 45, firing rod, 3 stages of planetary gearing, output gear on the motor shaft, and rotor, for example. Dynamic braking on the motor defines the stopping power the motor has due to a trigging point. At typical firing speeds through the middle portion of the firing stroke, and under various use conditions, backlash due to inertia may allow for 0.005"-0.050" (0.1 mm-1.3 mm) of firing assembly 61 travel before dynamic breaking can stop the inertia. In some embodiments, the start position XF of the end of stroke algorithm is determined at least in part on inertia of the firing assembly 61, transmission 66, and/or motor 63.

In some embodiments, to address the inconsistency due to the switch 47, and inertia of the firing assembly 61, transmission 66, and/or motor 63, the switch 47 can be positioned so that the end of stroke algorithm engages in time to decelerate the firing assembly 61 to the final, slow target speed before the distal portion of the firing assembly 61 impacts the end effector 40. In addition to including the switch 47, or as an alternative, the firing stroke algorithm can be configured to estimate a position of the distal end of the firing assembly 61 based on rotation of the motor 63 and/or position of the proximal end of the firing assembly 61. The end of stroke algorithm may be engaged based at least in part on the estimated position of the distal end of the firing assembly 61. The start position XF of the end of stroke algorithm can be based at least in part on this uncertainty so that the end of stroke algorithm engages in time to decelerate the firing assembly 61 to the final, slow target speed before the distal portion of the firing assembly 61 impacts the end effector 40.

In some embodiments, the actual start position in which the end of stroke algorithm is engaged may vary from one firing stroke to the next, and/or there may be some uncertainties in the actual start position. The end of stroke algorithm is configured to engage when the distal portion of the firing assembly 61 is at start position XF as indicated. The start position XF may be selected based on the various causes for variation and uncertainty so that the end of stroke algorithm engages in time to decelerate the firing assembly 61 to the final, slow target speed before the distal portion of the firing assembly 61 impacts the end effector 40.

In some embodiments, the firing stroke algorithm comprises a limiting trigger. In some embodiments, the speed of the firing assembly 61 is controlled based at least in part on the limiting trigger. In some embodiments, the firing stroke algorithm is configured to detect impact of the distal portion of the firing assembly 61 to the end effector 40 based at least in part on a measurement of the limiting trigger exceeding a threshold value in the final distance of the firing stroke. The limiting trigger can include a current draw by the motor 63 (FIGS. 6 and 7) of the motor assembly, a load force on the motor 63, a speed differential of the firing assembly 61, and/or a knife sensing system. A threshold value of the limiting trigger utilized by the end of stroke algorithm may be less than a threshold value of the limiting trigger in the middle distance of the firing stroke. In some embodiments, the end of stroke algorithm is configured to lower a force and/or current threshold limit through the final distance of the firing stroke. The limiting trigger can be configured so that impact of the distal portion of the firing assembly 61 with the end effector 40 can be tolerated by the system without causing failure of the surgical stapler 10. In some embodiments, the firing stroke algorithm is configured to cause the speed control circuit 71 (FIG. 6) to sample the limiting trigger at a greater sampling rate in the final distance dn, XN-XF compared to a sampling rate of the limiting trigger in a middle distance dm, xF-X1, d1 (FIGS. 5A, 5B, and 7) of the firing stroke.

The firing assembly 61 may also include a component configured to maintain the end effector 40 in a clamped configuration during a firing stroke. As illustrated, the I-beam 45 is configured to translate through respective channels in the anvil 41 and staple jaw 42 during a firing stroke to maintain the end effector 40 in the clamped configuration during the firing stroke. The firing assembly 61 can be modified to include additional or alternative components configured to maintain the end effector 40 in a clamped configuration during a firing stroke as understood by a person skilled in the pertinent art. In an alternative embodiment, the firing assembly 61 need not include a component configured to maintain the end effector 40 in a clamped configuration; and the powered surgical stapler 10 can be modified to include a clamping component that does not translate longitudinally during a firing stroke.

In some embodiments, the end of stroke algorithm is readily adaptable for multiple surgical stapler configurations. The end of stroke algorithm can be configured to receive information about configuration of the surgical stapler (e.g., type of stapler, type of reload), and set parameters of the end of stroke algorithm based on the surgical stapler configuration. Parameters of the end of stroke algorithm which may be set based on the surgical stapler configuration may include the target speed, the length of the final distance, and/or load threshold.

Figure 3A:
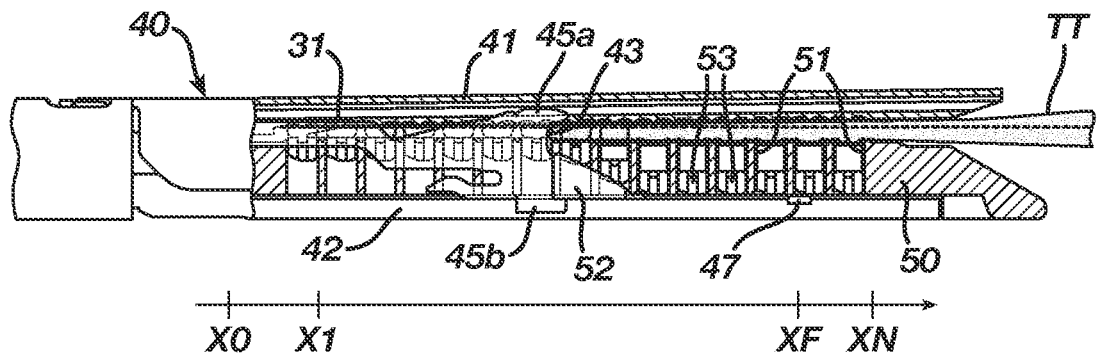
FIGS. 3A, 3B, and 3C are illustrations of the exemplary end effector of the exemplary powered surgical stapler at various stages of a firing stroke.
Figure 3B:
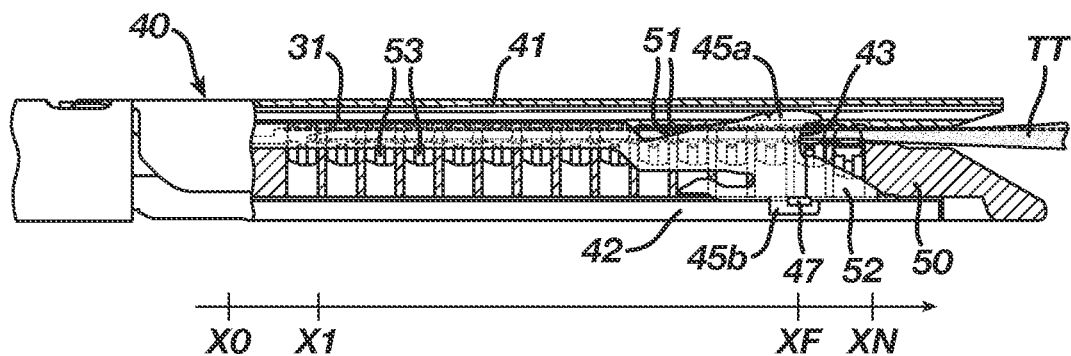
Figure 3C:
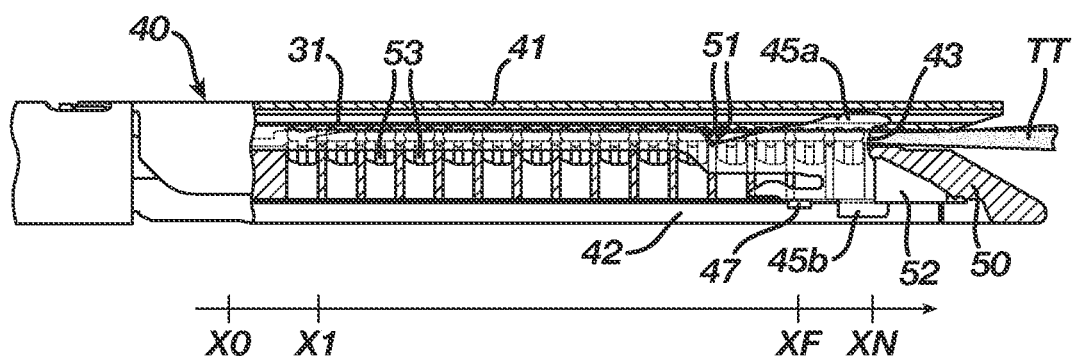

FIGS. 3A, 3B, and 3C are illustrations of the end effector 40 of the powered surgical stapler 10 at various stages of a firing stroke.

Figure 6:
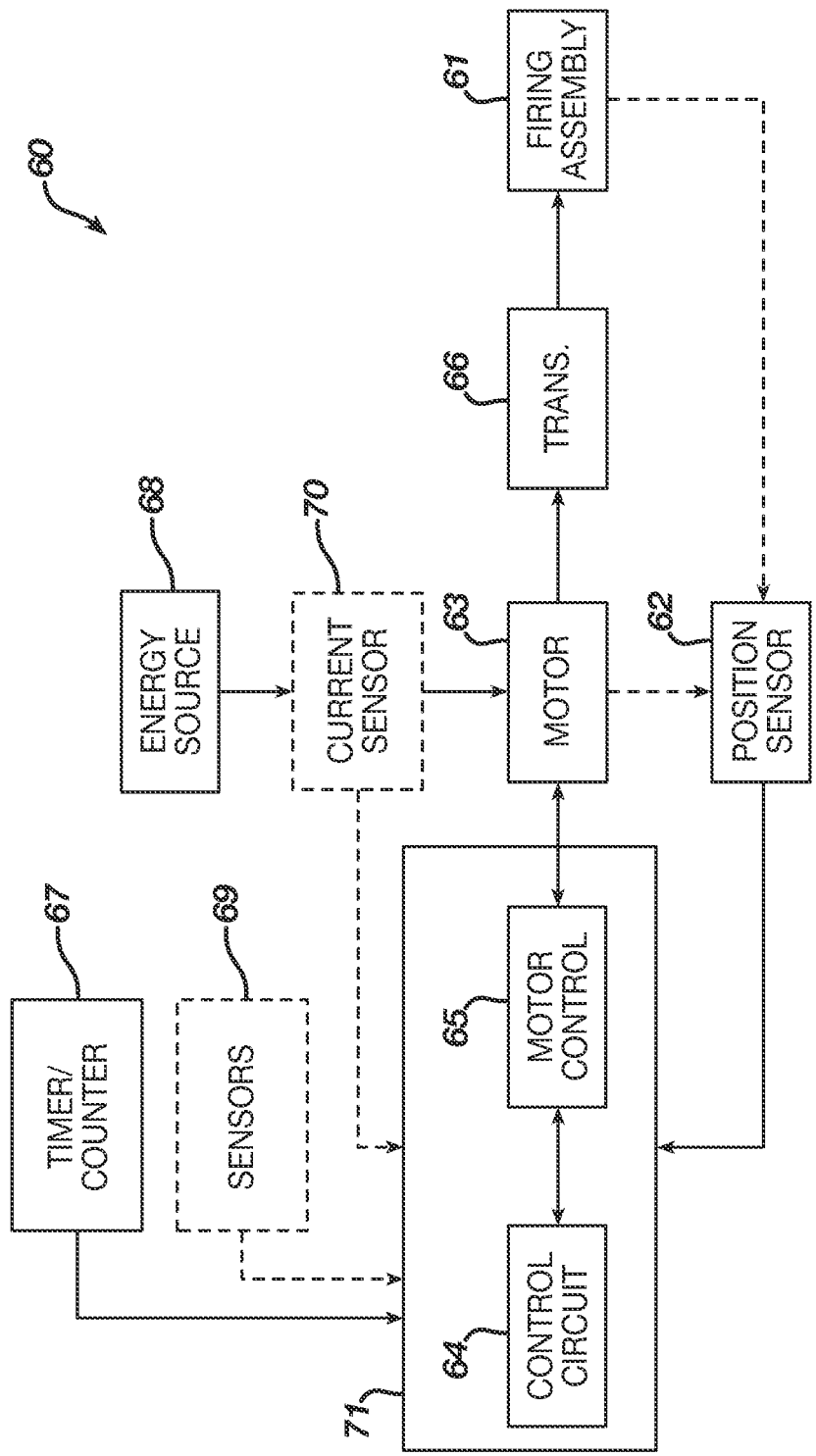
FIG. 6 is a block diagram of an exemplary firing driver for a powered surgical stapler.
Figure 7:
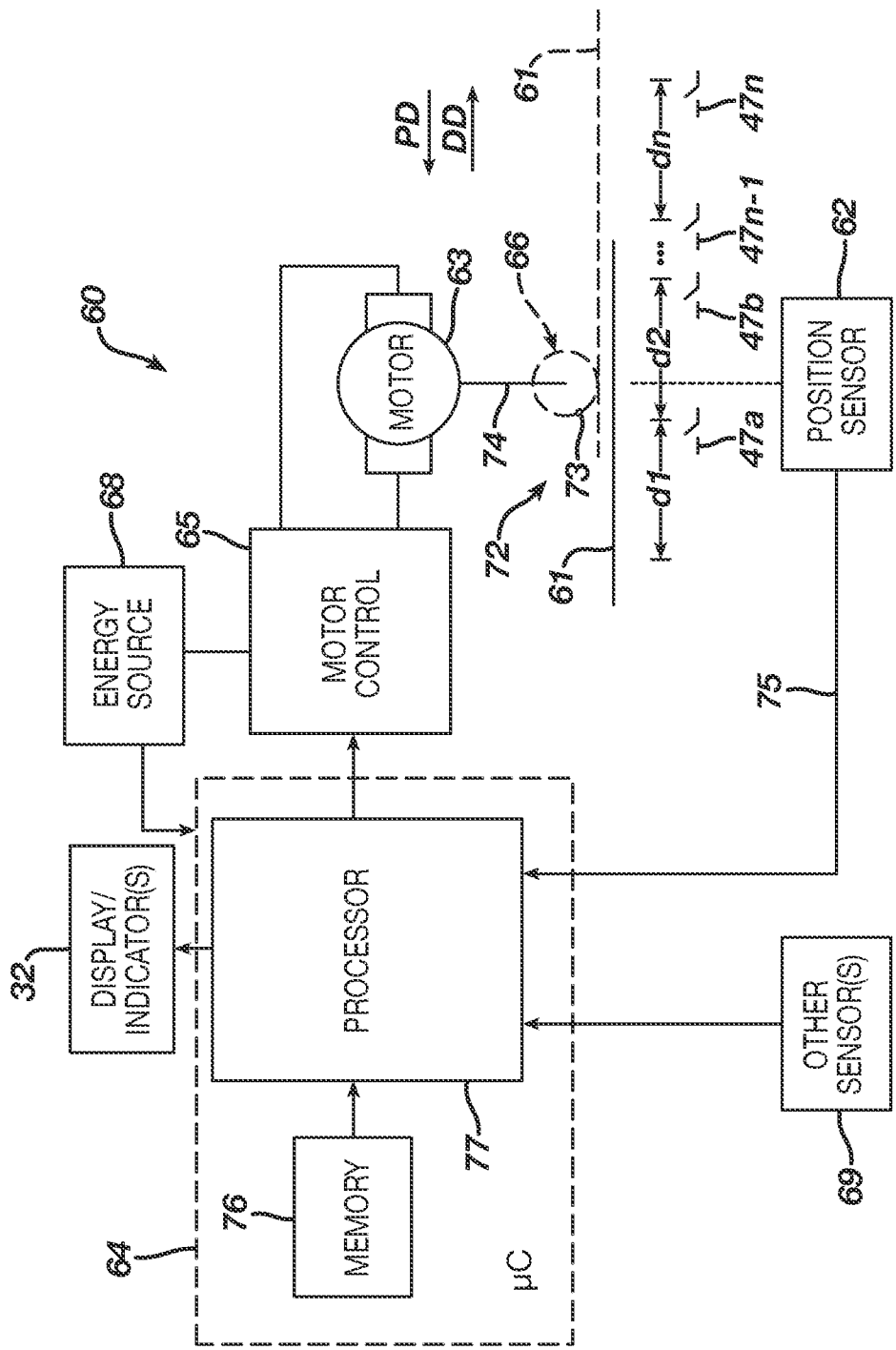
FIG. 7 is another block diagram of the exemplary firing driver.

FIG. 3A illustrates traveling the middle of the firing stroke. Upper and lower portions 45a, 45b of the I-beam 45 are engaged to the anvil 41 and staple jaw 42 to maintain closure of the end effector 40 on tissue TT. Staples 51 in a proximal direction PD of the wedge sled 52 are deployed into tissue TT, staples 51 in contact with the wedge sled 52 are in the process of being deployed, and staples 51 in a distal direction DD of the wedge sled 52 are not yet deployed. The firing assembly 61 is driven distally, and encounters resistance due to tissue properties. The resistance experienced by the firing assembly 61 can vary from one firing stroke to the next due at least in part to variation in tissue properties from one firing stroke to the next. The variation in resistance can affect firing speed and inertia of the firing assembly 61, transmission 66 (FIGS. 6 and 7), and motor 63 (FIGS. 6 and 7). The variation in resistance can also affect bowing of elongated structures such as the firing bar 31, which can cause an uncertainty in the position of the distal portion of the firing assembly 61 when calculated based on motor rotation and/or position of the proximal end of the firing assembly 61. In some embodiments, the location of the start point XF of the end of stroke algorithm takes into account this variation in resistance so that the end of stroke algorithm engages in time to decelerate the firing assembly 61 to the final, slow target speed before the distal portion of the firing assembly 61 impacts the end effector 40.

FIG. 3B illustrates the distal portion of the firing assembly 61 positioned at the start point XF of the end of stroke algorithm. As illustrated, the optional switch 47 closes in response to the distal portion of the firing assembly 61 crossing the switch 47. The end of stroke algorithm is engaged to slow the speed of the firing assembly 61 at this point.

FIG. 3C illustrates the distal portion of the firing assembly 61 positioned at the end position XN. At this position, the distal portion of the firing assembly 61 is in contact with the end effector 40. For instance, upper and/or lower portions 45a, 45b, may be in contact with an end of an I-beam channel in the anvil 41 and/or staple jaw 42, a distal angled surface of the wedge sled 52 may be in contact with an interior, proximally facing surface of the cartridge 50, resistance members (not illustrated) of the end effector 40 and/or firing assembly 61 may be in contact, or any combination thereof. The end effector 40 and firing assembly 61 may further have various alternative configurations not illustrated herein. Features of the firing assembly 61 can be in contact with the end effector 40 according to the design of the surgical stapler 10 as understood by a person skilled in the pertinent art.

Figure 4:
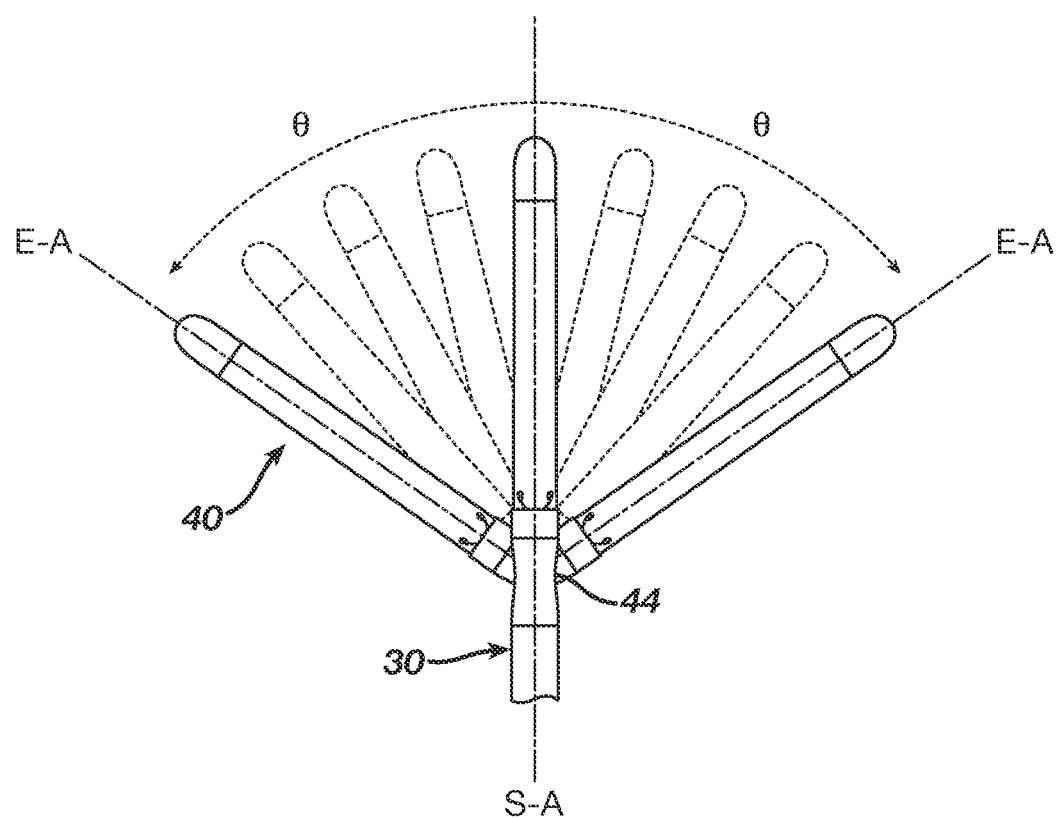
FIG. 4 is an illustration of articulation angles of the exemplary end effector.

FIG. 4 is an illustration of articulation of the end effector 40. The articulation joint 44 can bend to move the end effector 40 so that the longitudinal axis E-A of the end effector 40 is at an articulation angle θ to the longitudinal axis S-A of the shaft 30. The surgical stapler 10 includes one or more elongated structures, extending through the articulation joint 44 that may bend in response to articulation of the end effector 40. For instance, the firing bar 31 may bend at the articulation joint 44. In some embodiments, bending of the elongated structure(s) results in a variability or uncertainty of the position of the distal portion of the firing assembly 61 when determined based on motor rotation or position of a proximal end of the firing assembly 61. In some embodiments, position at which the end of stroke firing algorithm is engaged to decrease the target firing speed, the value of the decreased firing speed, the position of the switch 47, and/or limiting trigger configuration is based at least in part on the variability and/or uncertainty of position of the distal portion of the firing assembly 61 due to end effector articulation.

Many contemporary surgical staplers include a laminate firing bar member knives/I-beam as part of a firing assembly (e.g., firing assembly 61 or variation thereof). In embodiments including a laminate firing bar member, when the end effector of the device is articulated, the laminates skew and therefore effectively get longer. For a fixed firing rack difference, such a laminate firing bar member may experience 5 mm difference of distal knife/I-beam travel (55 mm vs 60 mm) for a 45 degree of articulation of the end effector. This variance is load dependent, speed dependent, and component dependent. The distance the I-beam travels not only impact the length the resulting cut, but also the completeness of the staples since the I-beam also pushes the sled which directly impact the distal most drivers and staple forms.

In some embodiments, the firing stroke algorithm includes more than one displacement triggering that change operational properties of the motor, depending on the configuration of the sensed cartridge configuration. In some embodiments, the trigger locations are adjusted based articulation angle.

Figure 5A:
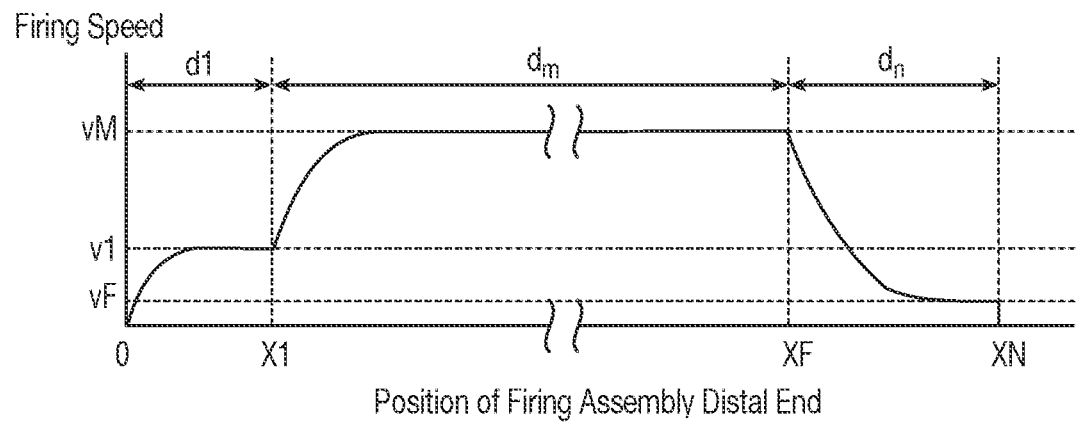
FIG. 5A is a plot of firing speed of a firing assembly of a powered surgical stapler as a function of a position of a distal end of the firing assembly.

FIG. 5A is a plot of firing speed of the firing assembly 61 (FIGS. 2, 6, and 7) as a function of a position of the distal portion of the firing assembly 61 for one example embodiment of a firing stroke algorithm. The firing assembly 61 is driven to an initial target speed v1 through an initial distance d1 of the firing stroke. The firing assembly 61 accelerates from a speed of zero to the initial target speed. The firing assembly 61 is driven to an increased target speed vM through a middle distance dm of the firing stroke that is distal to the initial distance d1. The increased target speed vM is greater than the initial target speed v1. The firing assembly 61 accelerates from the initial target speed v1 to the increased target speed vM. The firing assembly 61 is driven to a decreased target speed vF through a final distance dn of the firing stroke. The final distance dn is distal to the middle distance dm. The decreased target speed vF is less than the increased target speed vM. The decreased target speed vF is less than the initial target speed v1. The firing speed drops suddenly to zero at the end position XN due to impact of the distal portion of the firing assembly 61 to the end effector 40.

As illustrated, the firing assembly 61 remains consistently at the initial target speed v1, the increased target speed vM, and the decreased target speed vF after reaching the respective target speed. In reality, the speed of the firing assembly 61 may vary, and the speed of the firing assembly 61 may be dynamically adjusted toward the respective target speed. Meaning that, while the speed of the firing assembly 61 may not necessarily be consistently equal to the respective target speed, it is consistently being driven to the respective target speed in the various portions of the firing stroke.

Figure 5B:
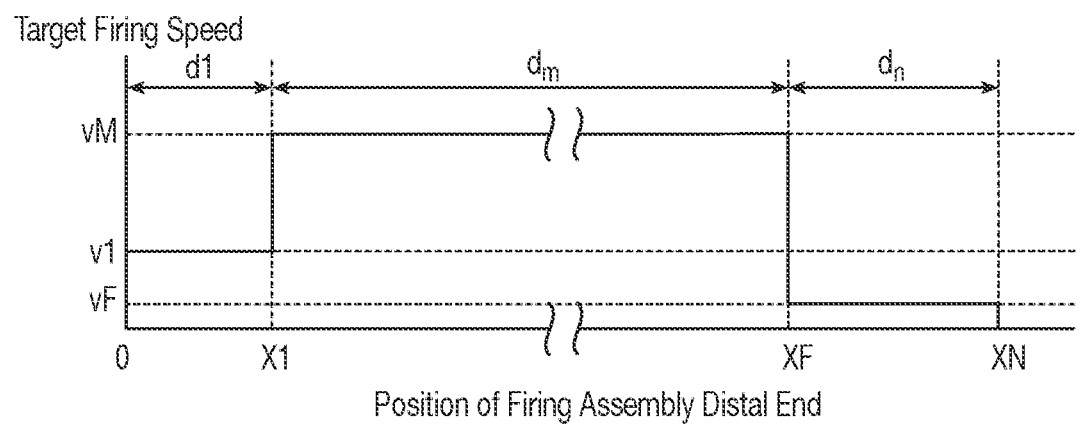
FIG. 5B is a plot of target firing speed as a function of the distal end of the firing assembly.

FIG. 5B is a plot of target firing speed as a function of the distal portion of the firing assembly 61 for the example embodiment of the firing stroke algorithm illustrated in FIG. 5A. The firing stroke algorithm sets the target speed to the initial target speed v1 through the initial distance d1 of the firing stroke. At the initial position X1, the firing stroke algorithm sets the target speed to the increased target speed vM. At the start position XF of the end of stroke algorithm, the target speed is decreased to the decreased target speed vF by the end of stroke algorithm. At the end position XN, the end of stroke algorithm detects an impact of the distal portion of the firing assembly 61 to the end effector 40 and ceases driving the firing assembly in response to detection of the impact. As illustrated, the end of stroke algorithm sets the target speed to zero at the end position XN.

FIG. 6 is block diagram of an example firing driver 60 for a powered surgical stapler such as the powered surgical stapler 10 illustrated in FIG. 1, variations thereof, or an alternative thereto as understood by a person skilled in the pertinent art. The firing driver 60 is configured to control longitudinal translation of a firing assembly 61 of the powered surgical stapler 10. The firing assembly 61 may include the firing bar 31, the knife 43, the I-beam 45, and the wedge sled 52 illustrated in FIG. 2, alternatives thereto, variations thereof, and/or sub combinations thereof as understood by a person skilled in the pertinent art. The firing assembly 61 is configured to deploy staples and cut tissue during a firing stroke of the powered surgical stapler 10. The firing driver 60 includes a speed control circuit 71 configured to drive a motor 63. The firing driver 60 includes a transmission 66 configured to convert the rotational movement of a rotor of the motor 63 into longitudinal movement of the firing assembly 61. The motor 63 and transmission 66 are collectively referred to herein as a motor assembly.

The speed control circuit 71 is configured with the firing stroke algorithm configured as disclosed herein, variations thereof, and alternatives thereto as understood by a person skilled in the pertinent art. The firing stroke algorithm is configured to engage the end of stroke algorithm to slow the speed of the firing assembly 61 through a final distance of the firing stroke, detect an impact of the distal portion of the firing assembly 61 to the end effector 40 (FIGS. 1-4), and cease driving the firing assembly 61 through the firing stroke in response to the detection of the impact.

The position, movement, displacement, and/or translation of one or more components of the firing assembly 61, can be measured by one or more position sensors 62. The position sensor(s) 62 may be configured to detect movement of the firing assembly 61 and/or rotation of the rotor of the motor 63. The position sensor(s) 62 can otherwise be configured to sense a physical parameter of the powered surgical stapler 10 and provide an electrical signal output indicative of the knife 43, I-beam 45, wedge sled 52, or other portion of the firing assembly 61 which translates longitudinally through the end effector 40 during a firing stroke. Additionally, or alternatively, the position sensor 62 can be configured to detect which staples 51 have been deployed and which have not been deployed. Deployment status of staples 51 may provide an indication of a position of the distal portion of the firing assembly 61.

The position sensor(s) 62 may be located in the end effector 40 and/or at any other portion of the powered surgical stapler 10. In some embodiments, the position sensor 62 includes an encoder configured to provide a series of pulses to the speed control circuit 71 as the rotor of the motor 63 rotates and the firing assembly 61 is translated longitudinally. The speed control circuit 71 may track the pulses to determine the position of a component of the firing assembly 61 (e.g., e.g., firing bar 31, the knife 43, I-beam 45, and/or wedge sled 52). Other suitable position sensor may be used, including, for example, a proximity sensor. Other types of position sensors may provide other signals indicating motion of a component of the firing assembly 61. In some embodiments, the position sensor 62 may be omitted. For instance, where the motor 63 is a stepper motor, the speed control circuit 71 may track the position of a component of the firing assembly 61 by aggregating the number and direction of steps that the motor 63 has been instructed to execute. In some embodiments, the position sensor(s) 62 may include a switch coupled to the end effector 40 configured similarly to switch 47 illustrated in FIGS. 2 and 3A through 3C.

In some embodiments, the end of stroke algorithm is configured to increase the frequency of monitoring the motor and/or firing assembly 61 by the position sensor(s) 62 in the final distance dn of the firing stroke.

Depending on the configuration of the position sensor(s) 62, position of the distal portion of the firing assembly 61 may be uncertain and/or vary from one firing stroke to the next. In some embodiments, position at which the end of stroke firing algorithm is engaged to decrease the target firing speed, the value of the decreased firing speed, the position of the switch 47, and/or limiting trigger configuration is based at least in part on the variability and/or uncertainty of position of the distal portion of the firing assembly 61 due to configuration of the position sensor(s) 62.

The speed control circuit 71 is illustrated as including a control circuit 64 and motor control 65, which are illustrated as two separate blocks. The control circuit 64 and motor control 65 and may be separate circuits or may be integrated as a single circuit. The control circuit 64 is configured to provide a motor setpoint signal output to the motor control 65. The motor setpoint signal is indicative of a target speed of the firing assembly 61. The motor controller 65 is configured to provide a motor drive signal to the motor 63 such that the motor drive signal is based on the motor setpoint signal and intended to drive the motor 63 so that the firing assembly 61 travels at the target speed.

The control circuit 64 and the motor controller 65 may include one or more processors and memory (i.e., one or more non-transitory computer-readable medium) with instructions that can be executed by the one or more processors to cause the control circuit 64 and the motor controller 65 to drive the motor 63. The memory can include the firing stroke algorithm and the end of stroke algorithm thereon as instructions that can be executed by the one or more processors.

In some embodiments, the control circuit 64 and/or motor controller 65 can include a feedback controller, which can be one of any feedback controllers, including, but not limited to a PID, a State Feedback, LQR, and/or an Adaptive controller, for example. The control circuit 64 and/or motor controller 65 can include a power source to convert the signal from the feedback controller into a physical input such as case voltage, pulse width modulated (PWM) voltage, frequency modulated voltage, current, torque, and/or force, for example.

The firing driver 60 includes a timer/counter circuit 67 configured to provide an output signal, such as elapsed time or a digital count, to the control circuit 64. In some embodiments, the control circuit 64 is configured to determine a position of the firing assembly 61 based on the signal from the position sensor(s) 62 and correlate the position of the firing assembly 61 with the output of the timer/counter circuit 67 such that the control circuit 64 can determine the position of one or more components of the firing assembly 61 (e.g. firing bar 31, the knife 43, I-beam 45, and/or wedge sled 52) at a specific time (t) relative to a starting position X0 (FIG. 2). The timer/counter circuit 67 may be configured to measure elapsed time, count external events, or time external events.

At the beginning of a firing stroke the control circuit 64 can be configured to provide a motor set point signal to the motor controller 65 that indicates the initial target speed v1. The motor controller 65 can be configured to provide a motor drive input signal to the motor 63 that adjusts power drawn by the motor 63 so that the motor 63 is accelerates to the initial target speed v1 and is driven approximately at the initial target speed v1.

In some embodiments, the motor 63 is driven by a pulse width modulated (PWM) electrical signal in which the duty cycle of the PWM signal can be adjusted by the motor controller 65 to vary power delivered to the motor 63. The motor controller 65 may include one or more circuits configured to provide a motor drive signal to the motor 63. In some embodiments, the motor 63 can include a brushless direct current (DC) electric motor and the motor controller 65 may provide a PWM motor drive signal to one or more stator windings of the motor 63.

In some embodiments, the motor controller 65 is configured to provide the PWM signal output to the motor 63 that has a fixed duty cycle corresponding to a target speed provided by the motor set point signal from the control circuit 64.

In some embodiments, the motor controller 65 may provide a variable duty cycle PWM signal output to the motor 63 that is adjusted based on speed error. For instance, the motor controller 65 can be configured to compare an actual speed of the firing assembly 61 to the target speed provided by the motor set point signal from the control circuit 64 and vary the duty cycle of the motor drive signal in response to error between the target speed and actual speed. The actual speed can be provided from the control circuit 64 and/or may be determined based on measurements from the position sensor(s) 62 and timer/counter circuit 67 as disclosed herein and otherwise understood by a person skilled in the pertinent art.

In some embodiments, the motor controller 65 includes a closed loop feedback system that adjusts or controls the duty cycle of the motor drive signal to adjust the speed of the firing assembly 61 based on a magnitude of one or more speed error terms over a specified increment of either time or distance. The error terms of interest may include, for example, short term, rate of change, steady state, and accumulated. Different error terms can be used in different zones (e.g., during acceleration, initial stabilization, and steady state). Different error terms can be magnified differently based on their importance within the algorithm.

In some embodiments, a closed loop on the motor controller 65 controls speed based on a limiting trigger. The motor controller 65 may utilize pulse width modulation, encoder based distance, rotation monitoring, or other such control mechanism to control speed based on the limiting trigger. The limiting trigger may be based on a force, a max current thru the motor circuit, a speed or time-to distance differential (PID real vs expected velocity control), a knife sensing system, other suitable metric, or sub-combination thereof. Such surgical stapler configuration may have a more precise trigger (i.e., more precise, or less dynamic breaking delay) compared to a surgical stapler utilizing switch logic. However, such surgical stapler configuration may have backlash due to inertial that may allow for 0.005"-0.050" (0.1 mm-1.3 mm) of I-beam travel before dynamic breaking can stop the I-beam momentum. In some embodiments, position at which the end of stroke firing algorithm is engaged to decrease the target firing speed, the value of the decreased firing speed, and/or limiting trigger configuration is based at least in part on the variability and/or uncertainty of position of the distal portion of the firing assembly 61 due to inertia of the firing assembly 61, transmission 66, and/or motor 63.

The control circuit 64 may optionally be in communication with one or more sensors 69. The sensors 69 may be positioned on the end effector 40 and configured to measure the various derived parameters such as gap distance versus time, tissue compression versus time, and anvil strain versus time. The sensors 69 may include a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 40.

The firing driver 60 may optionally include a current sensor 70 configured to measure the current drawn by the motor 63 from the energy source 68. In some embodiments, force required to advance the firing assembly 61 corresponds to the current drawn by the motor 63. In some embodiments, the firing stroke algorithm is configured to provide a force load on the motor during a firing stroke of up to about 200 lbf (about 890 N) longitudinal prior to engaging the end of stroke algorithm. In some embodiments the firing stroke algorithm is configured to drive the firing assembly 61 at speeds of about 5 mm/s to about 25 mm/s in thick tissue to about 30 mm/s in thin tissue prior to engaging the end of stroke algorithm. In some embodiments, the firing stroke algorithm is configured to drive the firing assembly at speeds greater than 30 mm/s prior to engaging the end of stroke algorithm.

In some embodiments, the firing stroke algorithm includes more than one displacement triggers that change operational properties of the motor, depending on the configuration of the sensed cartridge configuration. In some embodiments, the trigger locations are adjusted based articulation angle. In some embodiments, a lockout protection trigger is located at the beginning of the stroke. In some embodiments, an end of stroke trigger is located near the end of the total stroke of that cartridge configuration.

Regardless of the surgical stapler configuration (i.e. switch logic or other limiting trigger), the end of stroke algorithm may be configured to reduce the target speed of the firing assembly 61 in a portion of the firing stoke where a collision between the firing assembly 61 and end effector 40 (e.g. cartridge or channel) is intended to occur (i.e. at the end of the stoke of the firing assembly 61).

FIG. 7 is another block diagram of the exemplary firing driver 60. FIG. 7 illustrates additional and alternative aspects of the firing driver 60 illustrated in FIG. 6. The energy source 68, motor controller 65, motor 63, position sensor(s) 62, other sensor(s) 69, transmission 66, control circuit 64, and firing assembly 61 are configured as described in relation to FIG. 6. The firing driver 60 may also include a display or indicator(s) 32 configured to provide a visual or auditory indication to the user related to the operation of the firing driver 60. The control circuit 64 is illustrated as a micro-controller including a memory 76 and a processor 77. The firing stroke algorithm and end of stroke algorithm are stored as instructions in the memory 76 that can be executed by the processor 77 to cause the motor controller 65 to drive the firing assembly 61 to a target speed set by the firing stroke algorithm and the end of stroke algorithm.

The firing stroke algorithm and the end of stroke algorithm can utilize inputs from the position sensor(s) 62, other sensor(s) 69, energy source 68, and combinations thereof. As illustrated, the position sensor(s) 62 is configured with a sensor arrangement 72 including multiple sensors 47*a*, 47*b*, 47*n*-1, 47*n* coupled to the end effector 40 (FIGS. 1-4) each configured to provide an electrical signal to the control circuit 64. In some embodiments, the control circuit 64 is configured to determine a position of the distal portion of the firing assembly 61 based at least in part on a respective electrical signal from a respective sensor 47*a*, 47*b*, 47*n*-1, 47*n*. A sensor 47*a*, 47*b*, 47*n*-1, 47*n* may include a switch configured to close in response to the distal portion of the firing assembly 61 encountering the switch, or the sensor 47*a*, 47*b*, 47*n*-1, 47*n* may have an alternative sensor configuration, as understood by a person skilled in the pertinent art, that provides an electrical signal to indicate that the distal portion of the firing assembly 61 is positioned adjacent the switch. In some embodiments, the sensors 47*a*, 47*b*, 47*n*-1, 47*n* include magnetic sensor, analog rotary sensor like a potentiometer, array of analog Hall-effect elements, which output a unique combination of position signals or values, among others, for example.

The firing stroke may be divided into multiple zones d1, d2, dn, each defined over a portion of the length of the firing stroke. The sensors 47*a*, 47*b*, 47*n*-1, 47*n* are spaced apart on the end effector 40 along the length of firing stroke. The sensors 47*a*, 47*b*, 47*n*-1, 47*n* are positioned between the zones d1, d2, dn so that when the distal portion of the firing assembly 61 crosses a sensor, it moves into next zone distal of the senor.

In some embodiments, the firing stroke algorithm is configured to change operational parameters which dictate the firing stroke speed when crossing from one zone to the next. In some embodiments, the firing stroke algorithm changes a triggering limit and/or the target speed in portions of the firing stroke (e.g., in a lockout portion at the beginning of the firing stroke). In some embodiments the firing stroke algorithm changes the target speed and/or load/trigger thresholds due to encountered events within the firing stroke to allow for better, slower, or more controlled tissue compression which in turn limits the force-to-fire (FTF) and increased the reliability of the staples 51 to deploy good staples 51 and complete its stroke.

In some embodiments, the firing stroke algorithm is configured to detect an electrical signal from a sensor disposed approximate the distal end of the firing stroke, for instance sensor 47*n*-1, and engage the end of stroke algorithm in response to detecting the electrical signal from the sensor. In some embodiments, the end effector 40 includes a sensor positioned at the start point XF (FIGS. 2, 3A-3C, and 5A-5B) of the end of stroke algorithm. In some embodiments, the end effector 40 may lack any position sensors within the final distance dn. Alternatively, the end effector 40 may include a position sensor within the final distance dn. The distalmost sensor 47n can be positioned at the distal end of the firing stroke so that the distal portion of the firing assembly 61 causes the distalmost sensor 47n to send a signal to the control circuit 64 when the firing assembly 61 is at the end of the firing stroke. In some embodiments, the electrical signal from the distalmost sensor 47n is utilized to detect impact of the distal portion of the firing assembly 61 to the end effector 40. Detection of impact by the distalmost sensor 47n can be used in addition to, or in place of limiting triggers (e.g., motor current draw, speed differential, knife sensing, etc.).

As illustrated, a rotor 74 of the motor 63 is mechanically coupled to the transmission 66, and a sensor 73 (e.g., encoder) is configured to measure the rotational speed of the rotor 74. In addition to the sensor arrangement 72, or as an alternative, the approximate position of the distal portion of the firing assembly 61 can be calculated based measurement of the rotation of the motor 63 by sensor 73. In some embodiments the firing stroke algorithm includes displacement triggers which correspond to the positions of the distal portion of the firing assembly 61 during the firing stroke. In some embodiments, the displacement triggers are positioned such that the displacement triggers indicate when the approximate position of the distal portion of the firing assembly 61 crosses from one zone d1, d2 to the next dn. In some embodiments, the firing stroke algorithm is configured to change operational properties of the motor 63 based on which zone the approximate position of the distal portion of the firing assembly 61 is positioned in. In some embodiments, the positions of the displacement triggers are adjusted based on articulation angle. In some embodiments, a lockout protection trigger is located at the beginning of the stroke. In some embodiments, an end of stroke trigger is located near the end of the total stroke of that cartridge configuration.

The firing driver 60 may otherwise be configured with compatible features and functionality of an absolute positioning system such as illustrated in FIG. 100 of U.S. Pat. No. 10,828,028, incorporated by reference herein.

Figure 8:
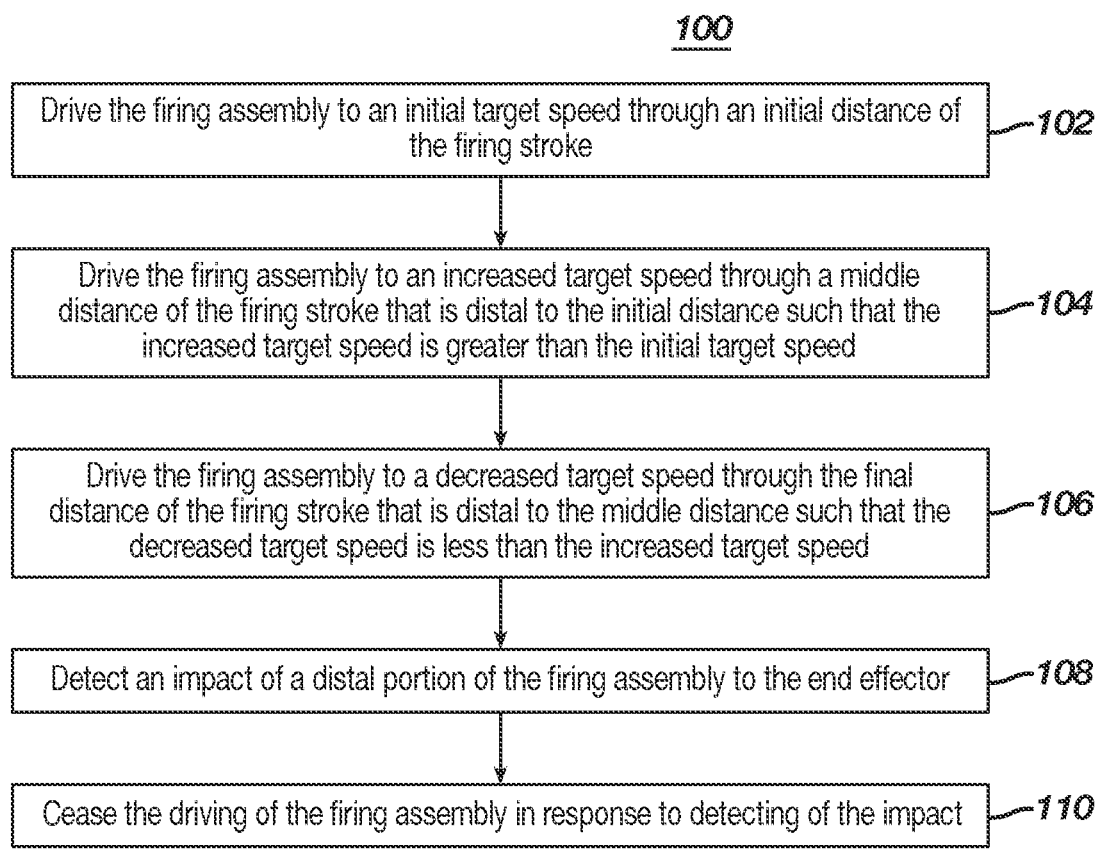
FIG. 8 is a flow diagram including steps of a method for controlling a firing stroke of a surgical stapler.

FIG. 8 is a flow diagram including steps of a method 100 for controlling a firing stroke of a surgical stapler 10. The method 100 can be realized in software for a surgical stapler such as the surgical stapler 10 illustrated in FIG. 1, alternative surgical staplers disclosed herein, variations thereof, and alternatives thereto as understood by a person skilled in the pertinent art. The method 100 can be stored as instructions in memory coupled to one or more processors of the surgical stapler 10 so that execution of the instructions controls the firing stroke of the surgical stapler 10 according to the method steps.

At block 102, the firing assembly is driven to an initial target speed v1 through an initial distance d1 of the firing stroke. The firing assembly can be configured similar to the firing assembly 61 disclosed herein, variations thereof, or alternatives thereto as understood by a person skilled in the pertinent art. The firing assembly may be driven by a speed control circuit configured similar to the speed control circuit 71 and/or control circuit 64 disclosed herein, variations thereof, or alternatives thereto as understood by a person skilled in the pertinent art.

At block 104, the firing assembly is driven to an increased target speed vM through a middle distance dm of the firing stroke that is distal to the initial distance d1 such that the increased target speed vM is greater than the initial target speed v1. The firing assembly can be driven to the increased target speed vM by a motor controller 65 similar to as disclosed herein, variations thereof, or alternatives thereto as understood by a person skilled in the pertinent art.

At block 106, the firing assembly is driven to a decreased target speed vF through a final distance dn of the firing stroke that is distal to the middle distance dm such that the decreased target speed vF is less than the increased target speed vM. The decreased target speed vF may further be less than the initial target speed v1.

At block 108, an impact of the distal portion of the firing assembly to the end effector 40 is detected. The impact may be detected by a limiting trigger or a sensor similar to as disclosed herein, variations thereof, or alternatives thereto, or otherwise detected as understood by a person skilled in the pertinent art.

At block 110, the firing assembly can cease being driven in response to detecting the impact.

The following clauses list non-limiting embodiments of the disclosure:

Clause 1. A powered surgical stapler comprising: a firing assembly configured to translate along a longitudinal axis such that translation of the firing assembly in a distal direction, during a firing stroke, is configured to deploy staples from an end effector; a motor assembly mechanically coupled to the firing assembly and configured to drive the firing assembly along the longitudinal axis; and a speed control circuit configured to: drive the firing assembly to an initial target speed through an initial distance of the firing stroke, drive the firing assembly to an increased target speed through a middle distance of the firing stroke that is distal to the initial distance such that the increased target speed is greater than the initial target speed, drive the firing assembly to a decreased target speed through a final distance of the firing stroke that is distal to the middle distance such that the decreased target speed is less than the increased target speed, detect an impact of a distal portion of the firing assembly to the end effector, and cease driving the firing assembly through the firing stroke in response to the detection of the impact.

Clause 2. The powered surgical stapler of clause 1, wherein the final distance is determined based at least in part on an inertia of the firing assembly and/or motor assembly.

Clause 3. The powered surgical stapler of clause 1 or 2, wherein the final distance is determined based at least in part on a dynamic braking capacity of the motor assembly.

Clause 4. The powered surgical stapler of any one of clauses 1-3, wherein the decreased target speed is based at least in part on a dynamic braking capacity of the motor assembly.

Clause 5. The powered surgical stapler of any one of clauses 1-4, wherein the final distance is determined based at least in part on an articulation angle of the end effector.

Clause 6. The powered surgical stapler of any one of clauses 1-5, wherein the speed control circuit is configured to set the decreased target speed based at least in part on a configuration of the end effector.

Clause 7. The powered surgical stapler of clause 6, wherein the firing assembly is configured to is configured to deploy staples from a cartridge during the firing stroke, wherein the configuration of the end effector comprises a cartridge comprising a cartridge type, and wherein the speed control circuit is configured to set the decreased target speed based at least in part on the cartridge type.

Clause 8. The powered surgical stapler of any one of clauses 1-7, wherein the speed control circuit is configured to set the final distance based at least in part on a cartridge type of a cartridge of the end effector.

Clause 9. The powered surgical stapler of any one of clauses 1-8, wherein the speed control circuit is configured to control speed of the firing assembly based at least in part on a limiting trigger, wherein the limiting trigger comprises at least one of a current draw by a motor of the motor assembly, a load force on the motor, a speed differential of the firing assembly, or a knife sensing system, and wherein a threshold value of the limiting trigger in the final distance of the firing stroke that is less than a threshold value of the limiting trigger in the middle distance of the firing stroke.

Clause 10. The powered surgical stapler of clause 9, wherein the speed control circuit is configured to detect the impact based at least in part on a measurement of the limiting trigger exceeding the threshold value in the final distance.

Clause 11. The powered surgical stapler of clause 9 or 10, wherein the speed control circuit is configured to sample the limiting trigger at a greater sampling rate in the final distance compared to a sampling rate of the limiting trigger in the middle distance.

Clause 12. The powered surgical stapler of any one of clauses 1-11, wherein the speed control circuit is configured to determine a position of the distal portion of the firing assembly based at least in part on an electrical signal from a switch coupled to the end effector, wherein the switch is configured to close in response to the distal portion of the firing assembly encountering the switch during the firing stroke, and wherein the speed control circuit is configured to drive the firing assembly to the decreased target speed in response to receiving an electrical signal from the switch indicating closure of the switch.

Clause 13. The powered surgical stapler of clause 12, wherein the final distance is determined based at least in part on variation in closure timing of the switch.

Clause 14. The powered surgical stapler of any one of clauses 1-13, wherein the decreased target speed is less than the initial speed.

Clause 15. The powered surgical stapler of any one of clauses 1-14, wherein the decreased target speed is about 2 mm/s to about 5 mm/s.

Clause 16. The powered surgical stapler of any one of clauses 1-15, wherein the final distance is about 15 mm to about 5 mm.

Clause 17. A method for controlling a firing stroke of a surgical stapler, the method comprising: driving the firing assembly to an initial target speed through an initial distance of the firing stroke; driving the firing assembly to an increased target speed through a middle distance of the firing stroke that is distal to the initial distance such that the increased target speed is greater than the initial target speed; driving the firing assembly to a decreased target speed through the final distance of the firing stroke that is distal to the middle distance such that the decreased target speed is less than the increased target speed; detecting an impact of a distal portion of the firing assembly to the end effector; and ceasing the driving of the firing assembly in response to detecting of the impact.

Clause 18. The method of clause 17, comprising: setting the final distance based at least in part on an inertia of the firing assembly and/or motor assembly.

Clause 19. The method of clause 17 or 18, comprising: setting the final distance based at least in part on a dynamic braking capacity of the motor assembly.

Clause 20. The method of any one of clauses 17-19, comprising: setting the decreased target speed based at least in part on a dynamic braking capacity of the motor assembly.

Clause 21. The method of any one of clauses 17-20, comprising: setting the final distance based at least in part on an articulation angle of the end effector.

Clause 22. The method of any one of clauses 17-21, comprising: setting the decreased target speed based at least in part on a cartridge type of a cartridge of the end effector, wherein the firing assembly is configured to is configured to deploy staples from the cartridge during the firing stroke.

Clause 23. The method of any one of clauses 17-22, comprising: setting the final distance based at least in part on a cartridge type of a cartridge of the end effector.

Clause 24. The method of any one of clauses 17-23, comprising: controlling the speed of the firing assembly during the firing stroke based at least in part on a limiting trigger, wherein the limiting trigger comprises at least one of a current draw by a motor the motor assembly, a load force on the motor, a speed differential of the firing assembly, or a knife sensing system, and wherein a threshold value of the limiting trigger in the final distance of the firing stroke is less than a threshold value of the limiting trigger in the middle distance of the firing stroke.

Clause 25. The method of clause 24, wherein detecting the impact of the distal portion of the firing assembly to the end effector comprises detecting a measurement of the limiting trigger exceeding the threshold value in the final distance.

Clause 26. The method of clause 24 or 25, comprising: sampling the limiting trigger at a greater sampling rate in the final distance compared to a sampling rate of the limiting trigger in the middle distance.

Clause 27. The method of any one of clauses 17-26, comprising: determining a position of the distal portion of the firing assembly based at least in part on an electrical signal from a switch coupled to the end effector, wherein the switch is configured to close in response to the distal portion of the firing assembly encountering the switch during the firing stroke; and driving the firing assembly to the decreased target speed in response to receiving an electrical signal from the switch indicating closure of the switch.

Clause 28. The method of clause 27, comprising: setting the final distance based at least in part on variation in closure timing of the switch.

Clause 29. The method of any one of clauses 17-28, wherein the decreased target speed is less than the initial speed.

Clause 30. The method of any one of clauses 17-29, wherein the decreased target speed is about 2 mm/s to about 5 mm/s.

Clause 31. The method of any one of clauses 17-30, wherein the final distance is about 15 mm to about 5 mm.

Having shown and described exemplary embodiments of the subject matter contained herein, further adaptations of the methods and systems described herein may be accomplished by appropriate modifications without departing from the scope of the claims. For instance, the end of stroke algorithm can be adapted for various powered surgical stapler types having a variety of cut lengths, inertial properties, sensor configurations, mechanical configurations for impact between the firing assembly and the end effector, etc. In addition, where methods and steps described above indicate certain events occurring in certain order, it is intended that certain steps do not have to be performed in the order described but, in any order, as long as the steps allow the embodiments to function for their intended purposes. Therefore, to the extent there are variations of the invention, which are within the spirit of the disclosure or equivalent to the inventions found in the claims, it is the intent that this patent will cover those variations as well. Some such modifications should be apparent to those skilled in the art. For instance, the examples, embodiments, geometrics, materials, component selections, component configurations, dimensions, ratios, steps, and the like discussed above are illustrative. Accordingly, the claims should not be limited to the specific details of structure and operation set forth in the written description and drawings.

What is claimed is:

1. A powered surgical stapler comprising:
 a firing assembly configured to translate along a longitudinal axis such that translation of the firing assembly in a distal direction, during a firing stroke, is configured to deploy staples from an end effector;
 a motor assembly mechanically coupled to the firing assembly and configured to drive the firing assembly along the longitudinal axis; and
 a speed control circuit configured to:
  drive the firing assembly to an initial target speed through an initial distance of the firing stroke,
  drive the firing assembly to an increased target speed through a middle distance of the firing stroke that is distal to the initial distance such that the increased target speed is greater than the initial target speed,
  drive the firing assembly to a decreased target speed through a final distance of the firing stroke that is distal to the middle distance such that the decreased target speed is less than the increased target speed,
  detect an impact of a distal portion of the firing assembly to the end effector, and
  cease driving the firing assembly in response to the detection of the impact.

2. The powered surgical stapler of claim 1, wherein the final distance is determined based at least in part on an inertia of the firing assembly and/or motor assembly.

3. The powered surgical stapler of claim 1, wherein the final distance is determined based at least in part on a dynamic braking capacity of the motor assembly.

4. The powered surgical stapler of claim 1, wherein the decreased target speed is based at least in part on a dynamic braking capacity of the motor assembly.

5. The powered surgical stapler of claim 1, wherein the final distance is determined based at least in part on an articulation angle of the end effector.

6. The powered surgical stapler of claim 1, wherein the speed control circuit is configured to set the decreased target speed based at least in part on a configuration of the end effector.

7. The powered surgical stapler of claim 6,
 wherein the firing assembly is configured to is configured to deploy staples from a cartridge during the firing stroke,
 wherein the configuration of the end effector comprises a cartridge comprising a cartridge type, and
 wherein the speed control circuit is configured to set the decreased target speed based at least in part on the cartridge type.

8. The powered surgical stapler of claim 1, wherein the speed control circuit is configured to set the final distance based at least in part on a cartridge type of a cartridge of the end effector.

9. The powered surgical stapler of claim 1,
 wherein the speed control circuit is configured to control speed of the firing assembly based at least in part on a limiting trigger,
 wherein the limiting trigger comprises at least one of a current draw by a motor of the motor assembly, a load force on the motor, a speed differential of the firing assembly, or a knife sensing system, and
 wherein a threshold value of the limiting trigger in the final distance of the firing stroke that is less than a threshold value of the limiting trigger in the middle distance of the firing stroke.

10. The powered surgical stapler of claim 9, wherein the speed control circuit is configured to detect the impact based at least in part on a measurement of the limiting trigger exceeding the threshold value in the final distance.

11. The powered surgical stapler of claim 9, wherein the speed control circuit is configured to sample the limiting trigger at a greater sampling rate in the final distance compared to a sampling rate of the limiting trigger in the middle distance.

12. The powered surgical stapler of claim 1,
 wherein the speed control circuit is configured to determine a position of the distal portion of the firing assembly based at least in part on an electrical signal from a switch coupled to the end effector,
 wherein the switch is configured to close in response to the distal portion of the firing assembly encountering the switch during the firing stroke, and
 wherein the speed control circuit is configured to drive the firing assembly to the decreased target speed in response to receiving an electrical signal from the switch indicating closure of the switch.

13. The powered surgical stapler of claim 12, wherein the final distance is determined based at least in part on variation in closure timing of the switch.

14. The powered surgical stapler of claim 1, wherein the decreased target speed is less than the initial target speed.

15. The powered surgical stapler of claim 1, wherein the decreased target speed is about 2 mm/s to about 5 mm/s.

16. The powered surgical stapler of any one of claim 1, wherein the final distance is about 15 mm to about 5 mm.

17. A method for controlling a firing stroke of a surgical stapler, the method comprising:
 driving a firing assembly to an initial target speed through an initial distance of the firing stroke;
 driving the firing assembly to an increased target speed through a middle distance of the firing stroke that is distal to the initial distance such that the increased target speed is greater than the initial target speed;
 driving the firing assembly to a decreased target speed through a final distance of the firing stroke that is distal to the middle distance such that the decreased target speed is less than the increased target speed;
 detecting an impact of a distal portion of the firing assembly to an end effector; and
 ceasing the driving of the firing assembly in response to detecting of the impact.

18. The method of claim 17, comprising:
 setting the final distance based at least in part on an inertia of the firing assembly and/or motor assembly.

19. The method of claim 17, comprising:
 setting the final distance based at least in part on a dynamic braking capacity of the motor assembly.

20. The method of claim 17, comprising:
 setting the decreased target speed based at least in part on a dynamic braking capacity of a motor assembly of the surgical stapler.

* * * * *